United States Patent [19]

Kloosterboer et al.

[11] Patent Number: 5,030,627

[45] Date of Patent: Jul. 9, 1991

[54] Δ⁴-19-SULFUR SUBSTITUTED-ANDROSTENE DERIVATIVES HAVING AROMATASE-INHIBITING ACTIVITY

[75] Inventors: Helenius J. Kloosterboer, Av Oss; Hubert J. J. Loozen, Ac Uden, both of Netherlands

[73] Assignee: Akzo N.V., Arnhem, Netherlands

[21] Appl. No.: 326,955

[22] Filed: Mar. 22, 1989

[30] Foreign Application Priority Data

Mar. 24, 1988 [NL] Netherlands ............... 8800735

[51] Int. Cl.⁵ .................. A61K 31/56; C07J 31/00
[52] U.S. Cl. .................. 514/182; 552/520; 552/632
[58] Field of Search .......... 260/397.2, 397.48, 397.43; 514/169, 184, 177, 178, 179, 182; 552/520, 632; 540/2, 106, 120

[56] References Cited

U.S. PATENT DOCUMENTS 4,473,564  9/1984  de Winter et al. ............ 552/632
4,634,694  1/1987  Loozen et al. ............ 260/397.4

FOREIGN PATENT DOCUMENTS 0149499  7/1985  European Pat. Off. .

Primary Examiner—Diana Rivers
Assistant Examiner—Yogendr Gupta
Attorney, Agent, or Firm—William M. Blackstone

[57] ABSTRACT

The invention relates to Δ⁴-androstene derivatives with aromatase-inhibiting activity having the formula:

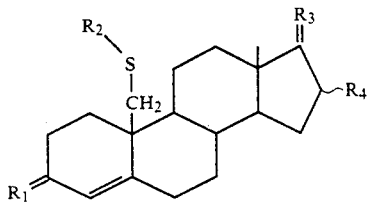

wherein
$R_1$ = O, ($\alpha R_5, \beta H$) or N—O—$R_6$;
$R_2$ = H, (1-12C)hydrocarbon radical, —SH, —S—(1-12C)-hydrocarbon radical or (1-12C)acyl;
$R_3$ = O or ($\alpha R_7, \beta R_8$);
$R_4$ = H or (1-12C)hydrocarbon radical;
$R_5$ = OH, O—(1-12C)hydrocarbon radical or O—(1-12C)acyl;
$R_6$ = H or (1-12C)hydrocarbon radical;
$R_7$ = H or (1-12C)hydrocarbon radical; and
$R_8$ = OH, O—(1-12C)acyl or O—(1-12C)hydrocarbon radical with the proviso that $R_1$ is not O if $R_4$ is H.

8 Claims, No Drawings

Δ⁴-19-SULFUR SUBSTITUTED-ANDROSTENE DERIVATIVES HAVING AROMATASE-INHIBITING ACTIVITY

The invention relates to novel Δ⁴-androstene derivatives, to methods for preparing said derivatives and to pharmaceutical formulations which contain said derivatives as active constituents.

Δ⁴-androstene derivatives are known from European patent 100,566 and European Patent Application 149,499. These derivatives exhibit aromatase-inhibiting activity.

Surprisingly, it has now been found that Δ⁴-androstene derivatives of the type described in the publications mentioned containing a 3α-O or 3-N substituent and/or a 16-C substituent exhibit an improved aromatase-inhibiting activity.

The invention therefore relates to Δ⁴-androstene derivatives having the formula:

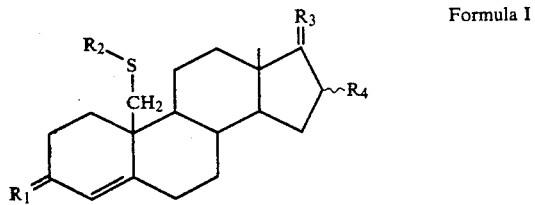

Formula I wherein
$R_1 = O$, $(\alpha R_5, \beta H)$ or $N—O—R_6$;
$R_2 = H$, (1-12C)hydrocarbon radical, —SH, —S—(1-12C)-hydrocarbon radical or (1-12C)acyl;
$R_3 = O$ or $(\alpha R_7, \beta R_8)$;
$R_4 = H$ or (1-12C)hydrocarbon radical;
$R_5 = OH$, O—(1-12C)hydrocarbon radical or O—(1-12C)acyl;
$R_6 = H$ or (1-12C)hydrocarbon radical;
$R_7 = H$ or (1-12C)hydrocarbon radical; and
$R_8 = OH$, O—(1-12C)acyl or O—(1-12C)hydrocarbon radical with the proviso that $R_1$ is not O if $R_4$ is H.

The (1-12C)hydrocarbon groups shown above can be branched or unbranched, saturated or unsaturated hydrocarbon radicals such as methyl, ethyl, ethenyl, ethynyl, propyl, isopropyl, cyclopentyl, propynyl, butyl, benzyl, octyl, decyl, 3-propylhexyl, cyclohexyl and 2,2-dimethylhexyl. The greatest preference is for hydrocarbon groups containing 1-4 carbon atoms. As regards $R_2$, $R_4$, $R_5$ and $R_8$, the hydrocarbon groups are, with still greater preference, alkyl groups containing 1-4 carbon atoms.

The (1-12C)acyl groups shown above are acyl groups derived from branched or unbranched, saturated or unsaturated carboxylic acids such as formic acid, acetic acid, propionic acid, butyric acid, isobutyric acid, trimethylacetic acid, phenylacetic acid, cyclopentylpropionic acid, cyclooctylacetic acid, fumaric acid, succinic acid, malonic acid, caproic acid, pelargonic acid and lauric acid. The greatest preference is for acyl groups containing 1-4 carbon atoms.

preferably, $R_2$ is H, (1-4C)alkyl, —SH, —S—(1-4C)-alkyl or —S—(1-4C)acyl and $R_4$ is H or (1-4C)alkyl and $R_5$ is OH or O—(1-4C)acyl and $R_6$ is H or (1-4C)alkyl and $R_7$ is H or a (1-4C)hydrocarbon radical and $R_8$ is OH or O—(1-4C)acyl.

The invention also relates to pharmaceutical formulations which contain one or more compounds according to the above formula I as active constituent. Such formulations are suitable, in particular, for inhibiting the aromatase activity. The compounds according to the invention are therefore primarily suitable for those clinical indications in which a suppression or reduction of the biosynthesis of oestrogens is desirable, such as in the case of women in the pre- and post-menopausal period to prevent or treat breast and/or uterine mucous membrane cancer and endometriosis, in anovulation resulting from obesity, in gynaecomastia, idiopathic oligospermia and in prostate hyperplasia.

The compounds according to the invention may be administered in the usual manner subcutaneously, intravenously, intramuscularly, orally, enterally or locally, in combination with pharmaceutical auxiliary substances, in the form of tablets, pills, dragees, powders, emulsions, suspensions, solutions, implants, creams, etc. Such pharmaceutical dosage forms are prepared by known galenical methods.

The compounds according to the invention in which $R_4$ is not H are prepared by reacting an androst-5-ene-3β,19-diol-17-one compound, in which the two OH groups are protected, with $R_4$ halide in the presence of a suitable base (for example, lithium diisopropylamide), preferably in an organic solvent and at a temperature of -70° to 25° C. The iodide is preferably used as halide. The protecting group for the 19-OH group is preferably an ether group and still more preferably a tetrahydropyranyl ether group, while the protecting group for the 3β-OH group is preferably a branched ester group such as pivaloyl. In this manner, a corresponding compound with an $R_4$ group in position 16 of the steroid skeleton is obtained.

Subsequently, the protecting group for the 3β-OH group is removed. In the case of an ester group, that can be achieved by reaction in the presence of hydroxide, for example NaOH or KOH, in an alcohol/water solvent. After an oxidation, for example an Oppenauer oxidation, (yields 3-keto, Δ⁴) the protecting group for the 19-OH group is removed, for example by reaction with an acid such as p-toluenesulphonic acid, in an organic solvent such as methanol.

In the 16-R₄-19-hydroxyandrost-4-ene -3,17-dione thus prepared, the hydroxyl group can subsequently be replaced by —S—R₂ in a manner known per se (see the European Patent Publications already mentioned). To prepare compounds in which $R_2$ is H, a hydrocarbon group or acyl, the 19-OH compound is converted into the corresponding 19-sulphonate by reaction with a sulphonic acid halide (reaction with tosyl chloride or mesyl chloride thus yields the corresponding 19-tosylate or 19-mesylate). Reaction of the 19-sulphonate with a metal salt of a hydrocarbon thiol or a thiocarboxylic acid yields respectively a 19-hydrocarbon thiol or a 19-acylthio compound according to the invention. If this last reaction is carried out with potassium thioacetate, the 19-acetylthio compound is obtained and this may appropriately be used to prepare—by means of hydrolysis—the corresponding 19-thiol. Reaction of the 19-thiol with a hydrocarbon halide yields corresponding 19-hydrocarbon-thio compounds. The 19-thiol compounds are also suitable for preparing compounds according to the invention in which $R_2$ is —SH or —S—(-hydrocarbon) in a similar manner to the methods described in the European patent Application 149,499, such as oxidative coupling to a mercapto compound or reaction With reactiVe alkylated disulphides in a basic medium. The androst-4-ene-3,17-dione compounds containing an $R_4$ group in position 16 and an $-S-R_2$ group in position 19 of the steroid skeleton and the corresponding compounds in which $R_4$ is H are used as the starting products for introducing $R_1$ and $R_3$ groups other than O:

1) The introduction of a 3α-OH group can be carried out by reaction with excess reducing agent in an organic solvent, for example with $NaBH_4$ in a $CH_3OH$/tetrahydrofuran mixture. This yields a corresponding compound containing 3α-OH and 17β-OH.

2) The introduction of a 3-N-O-$R_6$ groups takes place by selective reduction of the 17-O group by means of an inadequate quantity of $NaBH_4$ (yields 17β-OH), followed by reaction with $NH_2OR_6 \cdot HCl$ in an organic solvent. Oxidation, for example a Moffat oxidation, of the compound obtained again yields the 17-O compound.

3) 17α-$R_7$ groups in which $R_7$ is not H can be introduced by selective reduction of the 17-O group with an inadequate quantity of $NaBH_4$, followed by ketalization of the 3-O group (yields 3-ketal, $\Delta_5$-17β-OH) and by subsequently carrying out an oxidation (Moffat oxidation), a reaction with $R_7MgX$ (X=halogen) or $R_7Li$ and a deketalization, for example with HCl in acetone. In this manner, 19-S -$R_2$-17α-$R_7$-16-$R_4$-androst-4-ene-17β-ol-3-one compounds are obtained. Further reduction with $NaBH_4$ yields the corresponding 3α-OH compounds, while reaction with $NH_2OR_6 \cdot HCl$ yields the corresponding 3-N-O-$R_6$ compound.

In androst-4-ene-3,17-dione compounds containing an $-S-R_2$ group in position 19 of the steroid skeleton, an $R_4$ group may be introduced in position 16 by:

1) The reduction of a 17-O group with an inadequate quantity of $NaBH_4$; yielding a 17β-OH group, followed by protection of the 3-O group, e.g. by reaction with ethyleneglycol, followed by e.g. Oppenhauer oxidation of the 17β-OH group into a 17-O group.

2) The introduction of an $R_4$ group takes place by reaction with a suitable $R_4$ analogue, e.g. $R_4$-halogenide, in a strong basic medium.

3) Deprotection of the 3-O protective group yields the 19-S-$R_2$-16-$R_4$-androst-4-ene-3, 17-dione.

Preparation of compounds having a 3α-OH and 17-O group takes place, starting from the 3,17-diketal compound by partially reducing (yields 17β-OH), protecting the 17-OH group with an ether group, oxidizing the 17-OH group and, finally, deprotecting the 3-OH group in sequence.

In the compounds according to the invention prepared by the above methods, the hydroxyl groups in positions 3 and/or 17 may subsequently, if desired, be etherified or esterified by methods known per se, for example by reaction with a hydrocarbon halide or a carboxylic acid respectively or a functional derivative thereof, such as an anhydride.

The invention is explained in more detail on the basis of the following examples.

EXAMPLE 1

35.5 ml of a 1.55M butyllithium solution in hexane were added at −40° C. to a solution of 8.9 ml of diisopropylamine in 100 ml of dry tetrahydrofuran. Subsequently, a solution of 27 g of 3β-pivaloyl -19-(tetrahydropyran-2-yl)androst-5-ene-3β-ol-17-one in 200 ml of dry tetrahydrofuran was added at −70° C. After stirring for 15 min., a solution of 4 ml of methyl iodide in tetrahydrofuran (THF) was added. The stirring of the mixture was subsequently continued for 5 hours, the temperature being slowly raised to 20° C. The reaction mixture was poured out onto 2 litres of water and extracted with ethyl acetate. The organic layer was washed, dried and evaporated down. The residue was chromatographed using silica gel (toluene/ethyl acetate 9:1 v/v). This yielded 10.1 g of the corresponding 16-methyl compound; $R_f=0.40$ (toluene/ethyl acetate 7:3).

24 g of KOH and 200 ml of $CH_3OH/H_2O$ (1:1) were added to 36 g of this compound in 2 litres of methanol. The mixture was refluxed for 6 hours, evaporated down to approximately 500 ml and poured out onto 3 litres of $H_2O$. After extracting with $CH_2Cl_2$ and washing, drying and evaporating down the organic layer, chromatography was carried out using silica gel (toluene/ethyl acetate 7:3). This yielded 28 g of 19-tetrahydropyran-2-yl) -16-methylandrost-5-ene-3β-ol-17-one as an oil; $R_f=0.41$ (toluene/ethyl acetate 1:1).

A solution of 5.8 g of this compound, 3.75 g of aluminium isopropylate, 37 ml of cyclohexanone and 250 ml of dry toluene was refluxed for one hour. The reaction mixture was cooled down and poured out onto 1 litre of 5% $NH_4Cl$ solution. After extracting with ethyl acetate and washing, drying and evaporating down the organic layer, the residue was chromatographed using silica gel (toluene/ethyl acetate 2:1). This yielded 5 g of 19-(tetrahydropyran-2-yl)-16-methylandrost-4-ene-3,17-dione; $R_f=0.56$ (toluene/ethyl acetate 1:1).

1 g of p-toluenesulphonic acid was added to a solution of 26 g of this compound in 300 ml of methanol. The mixture was stirred for 4 hours. Subsequently, 20 ml of saturated $NaHCO_3$ solution was added, the reaction mixture was evaporated down to approximately 100 ml and poured out into 500 ml of $H_2O$. After extracting, washing, drying, evaporating down and chromatographing as already described above, 25 g of 16-methyl-19-hydroxyandrost-4 -ene-3,17-dione were obtained.

19 g of tosyl chloride were added to a solution of 19 g of this compound in 100 ml of pyridine. After stirring for 16 hours at room temperature, 50 ml of ice water was added and stirring was carried out for half-anhour at room temperature. The reaction mixture was poured out onto 500 ml of ice water and extraction was carried out with ethyl acetate. After washing, drying and evaporating down the organic layer it was chromatographed using silica gel (toluene/ethyl acetate 8:2). This yielded 17 g of 19-tosyloxy-16-methylandrost-4-ene-3,17-dione as an oil; $R_f=0.60$ (toluene/ethyl acetate 1:1).

Nitrogen was passed for 16 hours through a solution of 16 g of this compound in 160 ml of dimethyl formamide. Subsequently, 19 g of potassium thioacetate was added and the mixture was heated for 16 hours at 100° C. After pouring out onto 1 litre of $H_2O$, extracting with ethyl acetate, and washing, drying and evaporating down the organic layer, chromatography was carried out using silica gel. This yielded 6.7 g of 19-acetylthio-16-methylandrost-4-ene-3,17-dione; $R_f=0.45$ (toluene/ethyl acetate 8:2).

The corresponding 16-ethyl compound was obtained in a corresponding manner.

EXAMPLE 2

19 g of sodium methoxide were added to a solution of 6 g of the 16-methyl compound alternately obtained in Example 1 in 240 ml of $CH_3OH$. The reaction mixture was stirred for hour, poured out onto litre of $H_2O$, neutralized with acetic acid and extracted with ethyl acetate. The organic layer was washed with $H_2O$, dried and evaporated down. Chromatography using silica gel yielded 3.1 g of 19-mercapto-16-methylandrost-4-ene-3,17-dione; $R_f=0.55$ (hexane/ethyl acetate 1:1); melting point 130°–132° C.

The corresponding 16-ethyl compound was obtained in a corresponding manner.

EXAMPLE 3

0.14 ml of ethyl ethanethiosulphonate and then 30 mg of lithium amide were added to a solution of 332 mg of the 16-methyl compound obtained in Example 2 in 5 ml of dry tetrahydrofuran. After 15 min., the reaction mixture was poured out onto 20 ml of $H_2O$ and the product extracted with $CH_2Cl_2$. The organic layer was washed, dried and evaporated down. Chromatography of the residue yielded 0.17 g of 19-ethyldithio-16β-methylandrost-4-ene-3,17-dione ($R_f=0.52$, hexane/ethyl acetate and melting point 98° C.) and 0.16 g of 19-ethyldithio-16α-methylandrost-4-ene-3,17-dione ($R_f=0.43$, hexane/ethyl acetate 1:1 and melting point 89° C.

The corresponding 16β-methyl compound was obtained in a corresponding manner $R_f=0.52$ hexane/ethyl acetate 1:1), m.p 98° C.

The corresponding 16α-ethyl ($R_f=0.40$ toluene/ethyl acetate 9:1 and m.p. 89° C.) and 16β-ethyl compounds were obtained in a corresponding manner.

19-Ethylthio-16α-ethylandrost-4-ene-3,17-dione and the corresponding 16β-ethyl compound were obtained in a corresponding manner.

EXAMPLE 4

1.9 g of $NaBH_4$ were added at $-5°$ C. to a solution of 37.8 g of 19-ethyldithioandrost-4-ene-3, 17-dione in 400 ml of THF and 450 ml of $CH_3OH$. The reaction mixture was stirred for 0.5 hour at 0° C. and subsequently neutralized with 50% acetic acid. Subsequently, it was poured out onto 3 litres of $H_2O$ and extracted with $CH_2Cl_2$. The product thus obtained was chromatographed using silica gel (hexane/ethyl acetate 6:4). This yielded 25 g of 19-ethyldithioandrost-4-ene-17β-ol-3-one as a colourless oil.

In a comparable manner, starting from the compounds alternately prepared in the Examples 1, 2 and 3, the following compounds were obtained:
19-acetylthio-16-methylandrost-4-ene-17β-ol-3-one;
19-acetylthio-16-ethylandrost-4-ene-17β-ol-3-one;
19-mercapto-16-methylandrost-4-ene-17β-ol-3-one;
19-mercapto-16-ethylandrost-4-ene-17β-ol-3-one;
9-ethyldithio-16α-methylandrost-4-ene-17β-ol-3-one;
19-ethyldithio-16α-methylandrost-4-ene-17β-ol-3-one;
19-ethyldithio-16α-ethylandrost-4-ene-17β-ol-3-one; and
19-ethyldithio-16α-ethylandrost-4-ene-17β-ol-3-one.

EXAMPLE 5

3.3 g of $NH_2OH \cdot HCl$ were added to a solution of 1.5 g of 19-ethyldithioandrost-4-ene-17β-ol-3-one in 8 ml of pyridine. The reaction mixture was stirred for 2 hours at 80° C. and subsequently poured out onto 100 ml of $H_2O$, acidified with 2N HCl to pH 4 and subsequently extracted with $CH_2Cl_2$. The organic phase was washed with water, dried and evaporated down. After treating With ether, 1.6 g of 3-hydroxyimino-19-ethyldithioandrost-4-ene-17β-ol were obtained as a mixture of syn and anti oximes; melting point 125°–133° C.; $R_f=0.3$ (hexane/ethyl acetate 1:1).

The syn and anti oximes were obtained pure by chromatography using silica gel (toluene/ethyl acetate 5:15) and crystallization from isopropylether: syn oxime m.p. 149° C.; $R_f=0.36$ (toluene/ethyl acetate 1:1) and anti oxime m.p. 118° C.; $R_f=0.53$ (toluene/ethyl acetate 1).

The 3-oximes of the 16-alkyl compounds mentioned in Example 4 were prepared in an analogous manner.

EXAMPLE 6

1.14 g of dicyclohexylcarbodiimide and 0.4 ml of pyridine were added to a solution of 0.72 g of 3-hydroxyimino-19-ethyldithioandrost-4-ene-17β-ol in a mixture of 4.8 g of dry dimethylsulphoxide and 4.8 ml of dry toluene. The mixture was cooled and 0.17 ml of dichloroacetic acid was added dropwise at 5° C. After stirring for ½ hour at 5°–10° C., 0.2 ml of methanol was added dropwise, followed by a solution of 0.4 g of oxalic acid dihydrate in 3 ml of methanol. Subsequently 30 ml of ether were added to the mixture after ½ hour. The precipitate was filtered and the filtrate was washed with water with 10% $NaHCO_3$ solution and with water. The organic phase was subsequently dried and evaporated down. The residue was chromatographed using silica gel (hexane/ethyl acetate 8:2). This yielded 0.4 g of 3-synhydroxyimino-19-ethyldithioandrost-4-ene-17-one; melting point 91°–95° C. and $[\alpha\ _D{}^{20}=+266°$ (c=0.5; dioxane) and 3-anti-hydroxyimino-19-ethyldithioandrost-4-en-17-one.

The 17-one compounds of the 16-alkyl compounds mentioned in Example 5 were prepared in analogous manner.

EXAMPLE 7

In a similar manner to the method described in Example 4, the corresponding 17β-ol was prepared from 19-methylthioandrost-4-ene-3,17-dione. Subsequently, the 3-keto group was ketalyzed by means of an ethyleneglycol, triethylorthoformate and a catalytic quantity of acid with simultaneous rearrangement of double bond from the 4,5 to the 5,6 position. After a Moffat oxidation, a reaction with propynyl-MgBr and deketalyzation by means of HCl/acetone carried out in sequence, 19-methylthio-17α-(propyn-1-yl)androst-4-ene-17β-ol-3-one was obtained. Reduction With an excess of $NaBH_4$ in a manner similar to Example 4 yielded 19-methylthio-17α-(propyn-1-yl) androst-4-ene-3,17β-diol.

19-Ethyldithio-17α-(propyn-1-yl)androst-4-ene-3α,17β-diol (m.p. 105° C. and $R_f=0.29$ in hexane/acetone 2:1) and 19-ethyldithio-17α-(propyn-1-yl)-16-methylandrost-4-ene-3α,17β-diol were prepared in a corresponding manner.

EXAMPLE 8

0.6 g of $NaBH_4$ was added to a solution of 6 g of 19-methylthioandrost-4-ene-3,17-dione in a mixture of 25 ml of THF and 25 ml of methanol. After ½ hour, 2 ml of acetone, followed by 5 ml of 50% acetic acid were added. After stirring for ½ hour, the mixture was poured out into 200 ml of 5% $NaHCO_3$ solution. Subsequently, the product was extracted with $CH_2Cl_2$. After washing, drying and evaporating down the organic layer, the residue obtained was chromatographed using silica gel. In this manner, 4.8 g of 19-methylthioandrost-4-ene-3α,17β-diol were obtained, melting point 85°–87° C., ($R_f=0.23$ (toluene/ethyl acetate 7:3).

19-Ethyldithioandrost-4-ene-3α,17β-diol, melting point 106° C., $R_f=0.40$ (hexane/ethyl acetate 1:1), 19- mercaptoandrost-4-ene-3α,17β-diol, $R_f$=0.35 (hexane/ethyl acetate 1:1) and [α $_D^{20}$=250° (dioxane), 19-ethyldithio-16α-methylandrost-4-ene-3α,17β-diol, m.p. 146° C., $R_f$=0.40 (hexane/ethyl acetate 1:1), 19-ethyldithio-16β-methylandrost-4-ene -3α,17β-diol, m.p. 105° C., $R_f$=0.40 (hexane/ethyl acetate 1:1) and 19-ethy)-dithio-17-(1-propynyl)-androst-4-ene-3α,17β-diol, m.p. 105° C., $R_f$=0.29 (hexane/acetone 2:1) were prepared in a corresponding manner.

EXAMPLE 9

1 ml of propionic anhydride and 20 mg of 4-dimethylaminopyridine were added to a solution of 1 g of the 19-methylthio compound obtained in Example 8 in 10 ml of pyridine. The mixture was heated for 4 hours at 50°-60° C. After pouring out into 100 ml of ice water, stirring for 15 min and extracting with ether, the organic phase was washed, dried and evaporated down. The residue was chromatographed using silica gel. This yielded 1.1 g of 19-methylthioandrost-4-ene-3α,17β-diol 3,17-dipropionate, $[α]_D^{20}$= −0.6° (c=1, dioxane), $R_f$=0.57 (toluene/ethyl acetate 10:1).

In a similar manner was prepared 19-ethyldithioandrost -4-ene-3α,17β-diol 3,17-dipropionate, $[α]_D^{20}$= +20° (c=1, dioxane), $R_f$=0.45 (toluene/ethyl acetate 95:5).

EXAMPLE 10

To a solution of 50 g of 19-methylthioandrost-4-ene-3,17-dione in a mixture consisting of 250 ml of $CH_3OH$ and 100 ml of DHF was added 2,3 g of $NaBH_4$ at 0°-5° C. After stirring for 2 hours the reaction was complete and excess hydride was destroyed by addition of acetic acid. The reaction mixture was further diluted with 1½ liter of water and the product was extracted with ethyl acetate.

Upon concentration of the organic phase to a small volume, the product crystallized and was isolated by filtration, to give 33 g of 19-methylthioandrost-4-ene-17β-ol-3-one. $R_f$=0.40 (toluene/ethyl acetate 6:4).

EXAMPLE 11

A solution containing 33 g of the product of Example 10, 80 ml of ethylene glycol, 800 ml of benzene and 400 mg of p-toluenesulfonic acid was refluxed while removing water with a Dean-Stark separator. After 10 hours the reaction was complete and the mixture was washed several times with 10% $NaHCO_3$ solution.

After drying and concentration the residue was chromatographed over $SiO_2$ (toluene/ethyl acetate 85:15) and crystallized from toluene to provide 22 g of 3,3-ethylenedioxy-19-methylthioandrost-4-ene-17β-ol. $R_f$=0.55 (toluene/ethyl acetate 6:4).

EXAMPLE 12

The oxidation was carried out by refluxing a mixture consisting of 18 g of the product of Example 11, 750 ml of toluene, 22 g of Al-isopropylate and 95 ml of cyclohexanon for 1 hour. Then 120 g of potassium sodium tartrate was added, and the mixture was stirred for ½ hour at 50° C. Then reaction mixture was washed several times with water and the organic phase was dried and concentrated. The residue was treated with diisopropylether and solid product was filtered to give 15 g of 3,3-ethylenedioxy-19-methyl-thioandrost-4-ene-17-one. $R_f$=0.67 (toluene/ethyl acetate 6:4).

EXAMPLE 13

The alkylation of the product of Example 12 was performed by addition of a solution of 8 ml of 15% BuLi in hexane solution to a solution of 2 ml of diisopropylamine in 50 ml of THF at 0° C. to give lithiumdiisopropylamide. To this solution was added at −40° C. a solution of 5 g of the product of Example 12 in 30 ml of THF. After stirring for 10 min 2 ml of ethyliodide was added. The mixture was stirred for several hours and then worked up by addition of 400 ml of water. The aqueous mixture was extracted with ethyl acetate and the products were purified by chromatography over silica gel, using toluene/ethyl acetate 95:5 as eluent. This gave 1,3 g of 3,3-ethylenedioxy-16β-ethyl-19-methylthio-androst-4-ene-17-one ($R_f$=0.57 toluene/ethyl acetate 8:2) and 1,1 g of the 16α-ethyl isomer ($R_f$=0.50 toluene/ethyl acetate 8:2).

EXAMPLE 14

To a solution of 1,1 g of the 16α-ethyl isomer of Example 13 in 20 ml of acetone was added 0,6 ml of 6N HCl. After stirring for 1 hour the mixture was diluted with 100 ml of water and extracted with ethyl acetate. The organic phase was washed, dried and concentrated. The residue was purified by chromatography over silica gel, using toluene/ethyl acetate 9:1 as eluent. The product thus obtained was treated with diisopropyl ether, to give 720 mg of 19-methylthio-16α-ethyl-androst-4-ene-3,17-dione, melting point 83° C., $[α]_D^{20}$=132° (c=1; dioxane), $R_f$=0.55 (toluene/ethy acetate 7:3).

EXAMPLE 15

In an analogous manner was prepared ($R_f$ values in toluene/ethyl acetate 7:3, unless otherwise indicated; optical rotation determined with c=1 in dioxane):

19-methylthio-16β-octyl-androst-4-ene -3,17-dione; $R_f$=0,62, $[α]_D^{20}$= +140°, oil;

19-methylthio-16α-octyl-androst-4-ene-3, 17-dione; $R_f$=0,65, $[α]_D^{20}$= +96°, oil;

19-methylthio-16β-(2-propenyl)-androst-4-ene-3,17-dione; $R_f$=0,55, $[α]_D^{20}$= +182°, m.p. 130° C.;

19-methylthio-16α-(2-propenyl)-androst-4-ene-3,17-dione; $R_f$=0,60, $[α]_D^{20}$= +100°, m.p. 122° C.;

19-methylthio-16β-ethyl-androst-4-ene-3,17-dione; $R_f$=0,49, $[α]_D^{20}$= +179°, m.p. 120° C.;

19-methylthio-16α-methyl-androst-4-ene-3,17-dione; $R_f$=0,51, $[α]_D^{20}$= +165°, m.p. 144° C.;

19-ethylthio-16α-(2-propenyl)-androst-4-ene-3,17-dione; $R_f$=0,50, $[α]_D^{20}$= +100°, m.p. 112° C.;

19-ethylthio-16α-methyl-androst-4-ene-3,17-dione; $R_f$=0,43, (toluene/ethyl acetate 8:2), $[α]_D^{20}$= +170°, m.p. 102° C.;

19-ethylthio-16β-ethyl-androst-4-ene-3,17-dione; $R_f$=0,42, (toluene/ethyl acetate 8:2), $[α]_D^{20}$= +180°, m.p. 73° C.

EXAMPLE 16

A solution consisting of 1,5 g of 19-ethyldithioandrost-4-ene-17β-ol-3-one and 3,3 g of methoxylamine.HBr in 7 ml of pypiridine was heated at 80° C. for 2 hours.

The mixture Was diluted with 50 ml of water and extracted with $CH_2Cl_2$. The orqanic layer was washed several times with 2N hydrochloric acid and Water, dried an concentrated.

The residue was chromatographed over $SiO_2$, using hexane/ethyl acetate 1:1 as eluent, to give 0,96 g of 3-(E)-methoxyimino-19-ethyldithio-androst-4-ene-17β-ol, ($R_f$=0,36 (hexane/ethyl acetate 1:1) and 0,4 g of the Z-isomer ($R_f$=0,29 hexane/ethyl acetate 1:1).

EXAMPLE 17

To a solution of 0,95 g of 3-(E)-methoxyimino-19-ethyldithio-androst-4-ene-17β-ol in a mixture of 10 ml of DMSO and 2,6 ml of triethylamine was added 1,5 g of pyridine.SO₃ complex.

After stirring for ½hour 2,3 ml of isopropanol was added, stirred for 15 minutes, after which the reaction mixture was poured into 150 ml of water. The product was extracted with ethyl acetate. The organic layer was washed, dried and concentrated and the residue was purified by chromatography over silica gel (hexane/ethyl acetate 8:2) and the product was further purified by crystallization from ether/hexane to give 0,78 g of 3-(E)-methoxyimino-19-ethyldithio-androst -4-ene-17-one, $[\alpha]_D^{20}$=+285° (c=1, dioxane), m.p. 84°-86° C. In a similar was 3-(Z)-methoxyimino-19-ethyldithio-androst-4-ene-17-one was obtained, $[\alpha]_D^{20}$=+280° (c=½, dioxane), m.p. 137°-138° C., $R_f$=0,50 (hexane/ethyl acetate 1:1).

We claim:

1. Δ⁴-androstene derivatives having the formula:

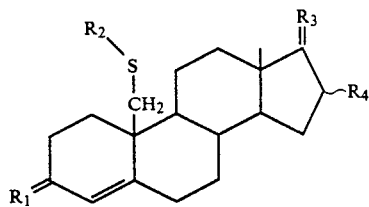

wherein
$R_1$=O, ($\alpha R_5$, $\beta H$) or N—O—$R_6$;
$R_2$=H or (1-12C) hydrocarbon radical;
$R_3$=O or ($\alpha R_7$, $\beta R_8$);
$R_4$=H or (1-12C) hydrocarbon radical;
$R_5$=OH, O-(1-12C) hydrocarbon radical or O-(1-12C)-acyl;
$R_6$=H or (1-12C) hydrocarbon radical;
$R_7$=H or (1-12C) hydrocarbon radical; and
$R_8$=OH, O-(1-12C) acyl or O-(1-12C) hydrocarbon radical with the proviso that $R_1$ is not O if $R_4$ is H.

2. Compound according to claim 1, wherein $R_2$=H or (1-4C)alkyl.

3. Compound according to claim 1, wherein $R_4$=H or (1-4C) alkyl.

4. Compound according to claim 1, wherein $R_5$=OH or O-(1-4C) acyl.

5. Compound according to claim 1, wherein $R_6$=H or (1-4C) alkyl.

6. Compound according to claim 1, wherein $R_7$=H or (1-4C) hydrocarbon radical.

7. Compound according to claim 1, wherein $R_8$=OH or O-(1-4C) acyl.

8. Pharmaceutical formulation comprising at least one compound according to claim 1 as active substance in an amount effective for inhibiting aromatase activity.

* * * * *